US007939317B1

(12) United States Patent
Gordon et al.

(10) Patent No.: US 7,939,317 B1
(45) Date of Patent: *May 10, 2011

(54) TRANSGENIC ANIMALS SECRETING DESIRED PROTEINS INTO MILK

(75) Inventors: Katherine Gordon, Boston, MA (US); Suzanne Groet, Sudbury, MA (US)

(73) Assignee: Genzyme Corporation, Framingham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 07/839,194

(22) Filed: Feb. 20, 1992

Related U.S. Application Data

(62) Division of application No. 07/441,785, filed on Nov. 27, 1989, now abandoned, which is a division of application No. 06/849,815, filed on Apr. 9, 1986, now abandoned.

(51) Int. Cl.
*C12N 15/00* (2006.01)
*C07H 21/02* (2006.01)
*C12P 21/00* (2006.01)
*A01K 67/027* (2006.01)

(52) U.S. Cl. ............ 435/320.1; 536/23.1; 800/4; 800/14

(58) Field of Classification Search ............... 435/320.1, 435/172.3; 536/27, 24.1, 23.1; 800/2, DIG. 1, 800/4, 14, 15, 16, 17, 18; 935/22, 48, 111
See application file for complete search history.

(56) References Cited

U.S. PATENT DOCUMENTS

| | | | |
|---|---|---|---|
| 4,495,280 A * | 1/1985 | Bujard et al. ................. 435/6 |
| 4,497,796 A | 2/1985 | Salser et al. |
| 4,512,922 A | 4/1985 | Jones et al. |
| 4,579,821 A | 4/1986 | Palmiter et al. |
| 4,696,898 A | 9/1987 | Fitts et al. |
| 4,736,866 A | 4/1988 | Leder et al. |
| 4,766,075 A | 8/1988 | Goeddel et al. |
| 4,873,316 A | 10/1989 | Meade et al. |
| 5,322,775 A * | 6/1994 | Clark et al. ................. 435/69.1 |
| 5,344,773 A | 9/1994 | Wei et al. |
| 5,366,894 A * | 11/1994 | Clark et al. |
| 5,476,995 A * | 12/1995 | Clark et al. ................ 800/16 |
| 5,827,690 A | 10/1998 | Meade et al. |
| 5,843,705 A | 12/1998 | DiTullio et al. |
| 5,849,992 A | 12/1998 | Meade et al. |
| 6,210,736 B1 | 4/2001 | Echelard et al. |
| 6,441,145 B1 | 8/2002 | DiTullio et al. |
| 6,448,469 B1 | 9/2002 | Smith |
| 6,472,584 B1 | 10/2002 | Smith |
| 6,528,699 B1 | 3/2003 | Meade et al. |
| 6,545,198 B1 | 4/2003 | Echelard et al. |
| 6,580,017 B1 | 6/2003 | Echelard et al. |
| 6,727,405 B1 * | 4/2004 | Gordon et al. ................ 800/14 |
| 6,743,966 B2 | 6/2004 | Smith |
| 7,019,193 B2 | 3/2006 | DiTullio et al. |
| 7,045,676 B1 * | 5/2006 | Gordon et al. ................ 800/14 |
| 2003/0005468 A1 | 1/2003 | Meade et al. |
| 2003/0046716 A1 | 3/2003 | Echelard et al. |
| 2003/0177513 A1 | 9/2003 | Echelard et al. |
| 2003/0204860 A1 | 10/2003 | Melican et al. |
| 2003/0213003 A1 | 11/2003 | Meade et al. |
| 2004/0006776 A1 | 1/2004 | Meade et al. |
| 2004/0025193 A1 | 2/2004 | Echelard et al. |
| 2004/0117863 A1 | 6/2004 | Edge et al. |
| 2004/0133931 A1 | 7/2004 | Gavin et al. |
| 2004/0148648 A1 | 7/2004 | Behboodi et al. |
| 2004/0205832 A1 | 10/2004 | Meade et al. |
| 2004/0226052 A1 | 11/2004 | Meade et al. |
| 2004/0226053 A1 | 11/2004 | Meade et al. |
| 2005/0060766 A1 | 3/2005 | Chen |
| 2005/0097625 A1 | 5/2005 | Meade et al. |
| 2005/0160483 A1 | 7/2005 | Meade et al. |
| 2005/0177882 A1 | 8/2005 | Gavin et al. |
| 2005/0186608 A1 | 8/2005 | Olsen |
| 2005/0193431 A1 | 9/2005 | Echelard et al. |
| 2006/0026695 A1 | 2/2006 | Edge et al. |
| 2006/0123500 A1 | 6/2006 | Echelard et al. |
| 2006/0168671 A1 | 7/2006 | Gavin et al. |
| 2006/0174359 A1 | 8/2006 | Melican et al. |
| 2006/0179493 A1 | 8/2006 | Meade et al. |
| 2006/0179500 A1 | 8/2006 | Meade et al. |
| 2006/0191025 A1 | 8/2006 | Echelard et al. |
| 2006/0191029 A1 | 8/2006 | Gavin et al. |
| 2008/0176786 A1 | 7/2008 | DiTullio et al. |

FOREIGN PATENT DOCUMENTS

| | | |
|---|---|---|
| EP | 0 105 141 A2 | 4/1984 |
| EP | 0 116 718 A1 | 8/1984 |
| EP | 0 117 060 A2 | 8/1984 |
| EP | 0 122 791 A1 | 10/1984 |
| EP | 0 131 623 A1 | 1/1985 |
| EP | 0 263 166 A1 | 4/1988 |
| EP | 0 264 166 B1 | 4/1988 |
| EP | 0 279 582 A2 | 8/1988 |
| EP | 0 791 652 A1 | 8/1997 |
| EP | 0 923 308 A1 | 6/1999 |

(Continued)

OTHER PUBLICATIONS

Palmita et al., Cell 41: 343-345 (1985).*
Roso et al., Proc. Natl. Acad. Sci; 82 : 5880-5884 (1985).*
Stewart et al., Cell 38: 627-637 (1984).*
Chisari et al., Science 230: 1157-1160 (1985).*
Andres et al., Experientia 42 (6): 673(1986).*
Pennica et al., Nature 301: 214-222(1983).*
Campbell et al., Nucleic Acid Res. 12 (22): 8685-8697 (1984).*
Yu-Lee et al (1986) Nucleic Acids Res. 14, 1883-1902.*
Campbell et al (1984) Nucleic Acids Res. 12, 8685-8697.*

(Continued)

*Primary Examiner* — Peter Paras, Jr.
*Assistant Examiner* — David Montanari
(74) *Attorney, Agent, or Firm* — Wolf, Greenfield & Sacks, P.C.

(57) ABSTRACT

A DNA sequence containing a gene encoding a protein, the gene being under the transcriptional control in the DNA sequence of a mammalian milk protein promoter which does not naturally control the transcription of the gene, such DNA sequence including DNA enabling secretion of the protein.

13 Claims, 5 Drawing Sheets

FOREIGN PATENT DOCUMENTS

| | | |
|---|---|---|
| WO | WO 82/04443 A1 | 12/1982 |
| WO | WO 88/00239 A1 | 1/1988 |
| WO | WO 88/01648 A1 | 3/1988 |

OTHER PUBLICATIONS

Qasba et al (1984) Nature 308, 377-380.*
Jones et al (1985) J. Biolog. Chem. 260, 7042-7050.*
Yu-Lee et al (1983) J. Biolog. Chem. 258, 10794-10804.*
Stewart et al (1984) Nucleic Acids Res. 12, 3895-3907.*
Kraemer et al "Gene Transfer into Pronuclei of Cattle and Sheep Zygotes".*
Hammer et al (1985) Nature 315, 680-683.*
Gordon et al (1987) Bio/Technology 5, 1183-1186.*
Gordon et al (1991) Bio/Technology 9, 835-838.*
Qasba et al., Similarity of the Nucleotide Sequences of Rat alpha-Lactalbumin and Chicken Lsozyme Genes, Nature, Mar. 22, 1985, vol. 308, pp. 377-380.*
Yu-Lee et al., Evolution of the Caein Multigene Family; Conserved Sequences in the 5' Flanking and Exon Regions, Nucleic Acid Res., vol. 14, No. 4, pp. 1883-1902.*
Jones et al. The Rat Casein Multigene Family, J. Biol. Chem., 1985, vol. 260, No. 11, pp. 7042-7050.*
Yu-Lee et al., The Rat Casein Multigene Family, J. Biol. Chem., 1983, vol. 258, No. 17, pp. 10794-10804.*
Ciliberto et al., Cell-Specifific Expression of a Transfected Human alpha-1-Antitrypsin Gene, Cell, 1985, vol. 41, pp. 531-540.*
Walker et al., Cell-Spcecific Expression Controlled by the 5'-Flanking Region of Insulin and Chymotrypsin Genes, Nature, 1983, vol. 306, pp. 557-561.*
Krumlauf et al., Developmental Regulation of alpha-Fetoprotein Genes in Transgenic Mice, Molec. Cell. Biol., 1985, vol. 5, No. 7, 1639-1648.*
Ott et al., Tissue-Specific Expression is Conferred by a Sequence from the 5' End of the Rat Albumin Gene, EMBO J., 1984, vol. 3, pp. 2505-2510.*
Ornitz et al., Specific Expression of an Elastase-Human Growth Hormone Fusion Gene in Pancreatic Acinar Cells of Transgenic Mice, Nature, 1985, vol. 313, pp. 600-602.*
Palmiter et al., Dramatic Growth of Mice that Develop from Eggs Microinjected with Metallothionein-Growth Hormone Fusion Genes, Nature, 300, pp. 611-615.*
Magram et al., Developmental Regulation of a Cloned Adult beta-globin Gene in Transgenic Mice, Nature, vol. 313, pp. 338-340.*
Ishii et al., Characterization and Sequence of the Promoter Region of the Human Epidermal Growth Factor Receptor Gene, Aug. 1985, Proc. Natl. Acad. Sci., vol. 82, 4920-4924.*
Melton et al., Structure, Expression and Mutation of the Hypoxanthine Phosphoribosyltransferase Gene, Apr. 1984, Proc. Natl. Acad. Sci., vol. 81, pp. 2147-2151.*
Reynolds et al., HMG CoA Reductase: A Negatively Regulated Gene with Unusual Promoter and 5' Untranslated Regions, 1984, Cell, vol. 38, pp. 275-285.*
Valerio et al. Adenosine Deaminase: Characterization and Expression-of a Gene with a Remarkable Promoter, EMBO J., 1985, vol. 4, No. 2, pp. 437-443.*
Pittius et al. PNAS 85:5874-5878 (Aug. 1988).*
Qasba et al., 1984, Nature, vol. 308, pp. 377-380.*
Animal Pharm Nov. 1, 1985 91:20.
Biotechnology Newswatch. McGraw-Hill, 1986;4.
[No Author] Churchill's Illustrated Medical Dictionary. New York: Churchill Livingstone, pp. 661 and 960, Oct. 12, 1989.
Genetic Manipulation of the Early Mammalian Embryo. Cold Spring Harbor Laboratory, 1985.
Andres et al., H-ras induced transformation of mammary epithelium is favoured by increased oncogene expression or by inhibition of mammary regression. Oncogene. May 1991;6(5):771-9.
Brinster et al., Introduction of genes into the germ line of animals.The Harvey Lectures, Series 80. 1986;1-38.
Bühler et al., Rabbit beta-casein promoter directs secretion of human interleukin-2 into the milk of transgenic rabbits. Biotechnology (N Y). Feb. 1990;8(2):140-3.
Bytebier et al., T-DNA organization in tumor cultures and transgenic plants of the monocotyledon Asparagus officinalis. Proc Natl Acad Sci U S A. Aug. 1987;84(15):5345-5349.
Castro et al., Transgenic rabbits for the production of biologically-active recombinant proteins in the milk. Genet Anal. Nov. 1999;15(3-5):179-87. Review.
Chada et al., Tissue- and stage-specific expression of a cloned adult beta globin gene in transgenic mice. Prog Clin Biol Res. 1985;191:305-19.
Chilton et al., Tailoring the agrobacterium ti plasmid as a vector for plant genetic engineering. Stadler Symposium. University of Missouri, Columbia, MO. 1981;13:39-52.
Church et al., Embryo manipulation and gene transfer in livestock. Can J Anim Schi Sep. 1985;65:527-538.
Clark et al., Expression of human anti-hemophilic factor IX in the milk of transgenic sheep. Bio/Technology. 1989;7:487-492.
Clark et al., Pharmaceuticals from transgenic livestock. Tibtech. Jan. 1987;5:20-24.
Clark, The mammary gland as a bioreactor: expression, processing, and production of recombinant proteins. J Mammary Gland Biol Neoplasia. Jul. 1998;3(3):337-50. Review.
Cocking et al., Aspects of plant genetic manipulation. Nature. 1981;293:265-9.
Dale et al., High-level expression of the rat whey acidic protein gene is mediated by elements in the promoter and 3' untranslated region. Mol Cell Biol. Mar. 1992;12(3):905-14.
De Cleene et al., The host range of crown gall. Bot Review. 1976;42:389-466.
De Framond et al., Mini-ti plasmid and a chimeric gene construct: new approaches to plant gene vector construction. Proceedings of the Miami Winter Symposium. 1983;20:159-170.
Dalrymple et al., Genetically modified livestock for the production of human proteins in milk. Biotechnol Genet Eng Rev. 1998;15:33-49. Review.
Deng et al., Science in China (Series B). 1990;33(1):27-34.
Denman et al., Transgenic expression of a variant of human tissue-type plasminogen activator in goat milk: purification and characterization of the recombinant enzyme. Biotechnology (N Y). Sep. 1991;9(9):839-43.
Drohan, The past, present and future of transgenic bioreactors. Thromb Haemost. Jul. 1997;78(1):543-7. Review.
Durnam et al., Isolation and characterization of the mouse metallothionein-I gene. Proc Natl Acad Sci U S A. Nov. 1980;77(11):6511-5.
Ebert et al., Transgenic production of a variant of human tissue-type plasminogen activator in goat milk: generation of transgenic goats and analysis of expression. Biotechnology (N Y). Sep. 1991;9(9):835-8.
Echelard et al., Chapter 24: Protein production in transgenic animals. S.C. Makrides, ed., Gene Transfer and Expression in Mammalian Cells. 2003:625-639.
Echelard et al., Chapter 11: The First Biopharmaceutical from Transgenic Animals: Atryn®. In Modern Biopharmaceuticals, eds. J. Knablein and R.H. Miler. 2005;1-26.
Echelard, Recombinant protein production in transgenic animals. Curr Opin Biotechnol. Oct. 1996;7(5):536-40. Review.
Edlund et al., Cell-specific expression of the rat insulin gene: evidence for role of two distinct 5' flanking elements. Science. Nov. 22, 1985;230(4728):912-6.
Fraley et al., Use of a chimeric gene to confer antibiotic resistance to plant cells. Proceedings of the Miami Winter Symposium. Miami Winter Symposia. Jan. 1983;20:211-221.
Goldsbrough et al., Expression of maize zein genes in transformed sunflower cells. Mol Gen Genet. 1986;202:374-381.
Gordon et al., Gene transfer into mouse embryos. Dev Biol (N Y 1985). 1986;4:1-36. Review.
Gordon et al., Gene transfer into mouse embryos: production of transgenic mice by pronuclear injection. Methods Enzymol. 1983;101:411-33.
Graves et al., The transformation of *Zea mays* seedlings with *Agrobacterium tumefaciens*, Plant Mol. Biol. 1986;7:43-50.

Graves et al., *Agrobacterium tumefaciens*-mediated transformation of the monocot genus *Gladiolus*: detection of expression of T-DNA-encoded genes. J Bacteriol. Apr. 1987;169(4):1745-6.

Gunzburg et al., A mammary-specific promoter directs expression of growth hormone not only to the mammary gland, but also to Bergman glia cells in transgenic mice. Mol Endocrinol. Jan. 1991;5(1):123-33. Abstract Only.

Hanahan, Heritable formation of pancreatic beta-cell tumours in transgenic mice expressing recombinant insulin/simian virus 40 oncogenes. Nature. May 9-15, 1985;315(6015):115-22.

Hansson et al., Expression and characterization of biologically active human extracellular superoxide dismutase in milk of transgenic mice. J Biol Chem. Feb. 18, 1994;269(7):5358-63.

Hennighausen et al., Characterization and cloning of the mRNAs specific for the lactating mouse mammary gland. Eur J Biochem. Jun. 15, 1982;125(1):131-41.

Herrera-Estrella et al., Expression of chimeric genes transferred into plant cells using a Ti-plasmid-derived vector. Nature. May 1983;303:209-213.

Hiei et al., Efficient transformation of rice (*Oryza sativa* L.) mediated by Agrobacterium and sequence analysis of the boundaries of the T-DNA. Plant J. Aug. 1994;6(2):271-82.

Hobbs et al., Sequence of rat alpha- and gamma-casein mRNAs: evolutionary comparison of the calcium-dependent rat casein multigene family. Nucleic Acids Res. Dec. 20, 1982;10(24):8079-98.

Hooykaas Van Slogteren et al., Expression of Ti-plasmid genes in monocotyledonous plants infected with *Agrobacterium umefaciens*. Nature. 1984;311:763-764.

Houdebine, Production of pharmaceutical proteins from transgenic animals. Biotechnol. May 31, 1994;34(3):269-87. Review.

Houdebine, The production of pharmaceutical proteins from the milk of transgenic animals. Reprod Nutr Dev. 1995;35(6):609-17. Review.

Huszar et al., Insertion of a bacterial gene into the mouse germ line using an infectious retrovirus vector. Proc Natl Acad Sci U S A. Dec. 1985;82(24):8587-91.

Ingram et al., alpha-Fetoprotein and albumin genes are in tandem in the mouse genome. Proc Natl Acad Sci U S A. Aug. 1981;78(8):4694-8.

Jänne et al., Transgenic animals as bioproducers of therapeutic proteins. Ann Med. Aug. 1992;24(4):273-80. Review.

Jänne et al., Transgenic bioreactors. Int J Biochem. Jul. 1994;26(7):859-70. Review.

Kemp et al., Oral presentation. Genetic Engineering: Applications to Agriculture symposium. May 16-19, 1982. Beltsville Agricultural Research Center. Beltsville, MD.

Kemp et al., Transfer of a functional gene via the Ti plasmid. Curr Top Plant Biochem Physiol. Proc Inaug Plant Biochem Physiol. Symp. Randal Douglas et al., eds. University of Missouri, Columbia, MO. 1982 (published 1983);1:170-179.

Khillan et al., Developmental and tissue-specific expression directed by the alpha 2 type I collagen promoter in transgenic mice. Proc Natl Acad Sci U S A. Feb. 1986;83(3):725-9.

Krieg et al., Efficient expression of cloned complementary DNAs for secretory proteins after injection into *Xenopus oocytes*. J Mol Biol. Dec. 15, 1984;180(3):615-43.

Lacy et al., A foreign beta-globin gene in transgenic mice: integration at abnormal chromosomal positions and expression in inappropriate tissues. Cell. Sep. 1983;34(2):343-58.

Lathe et al., Chapter 10 of Exploiting New Technologies in Animal Breeding: Genetic Developments. 1986;91-102.

Lee et al., Expression of the Rat β-Casein Gene in Transgenic Mice. Abstract presented at 26$^{th}$ Annual Meeting of the American Society for Cell Biology. Dec. 1986;313a. Abstract 1161.

Loveil-Badge, Transgenic animals: new advances in the field. Nature. Jun. 20, 1985;315:628-29.

Maga et al., Mammary gland expression of transgenes and the potential for altering the properties of milk Biotechnology (N Y). Dec. 1995;13(13):1452-7. Review.

Mahon et al., Oncogenesis of the lens in transgenic mice. Science. Mar. 27, 1987;235(4796):1622-8.

Marx et al., A Transposable Element of Maize Emerges. Science. Feb. 18, 1983;219(4586):829-830.

May et al., Generation of transgenic banana (*Musa cuminate*) plants via *agrobacterium*-mediated transformation. Biotechnology. 1995;13:486-492.

Meade et al., Bovine alpha S1-casein gene sequences direct high level expression of active human urokinase in mouse milk. Biotechnology (N Y). May 1990;8(5):443-6.

Overbeek et al., Lens-specific expression and developmental regulation of the bacterial chloramphenicol acetyltransferase gene driven by the murine alpha A-crystallin promoter in transgenic mice. Proc Natl Acad Sci U S A. Dec. 1985;82(23):7815-9.

Paleyanda et al., Regulation of human protein C gene expression by the mouse WAP promoter. Transgenic Res. Nov. 1994;3(6):335-43. Abstract Only. Erratum in: Transgenic Res. May 1995;4(3):following table of contents.

Paleyanda et al., Secretion of human furin into mouse milk. J Biol Chem. Jun. 13, 1997;272(24):15270-4.

Paleyanda et al., Transgenic pigs produce functional human factor VIII in milk. Nat Biotechnol. Oct. 1997;15(10):971-5.

Palmiter et al., Differential regulation of metallothionein-thymidine kinase fusion genes in transgenic mice and their offspring. Cell. Jun. 1982;29(2):701-10.

Palmiter et al., Germ-line transformation of mice. Annu Rev Genet. 1986;20:465-99. Review.

Palmiter et al., Metallothionein-human GH fusion genes stimulate growth of mice. Science. Nov. 18, 1983;222(4625):809-14. Review.

Patton et al., Intramammary infusion technique for genetic engineering of the mammary gland. J Dairy Sci. Jun. 1984;67(6):1323-6.

Piletz et al., Biochemical characterization of a novel whey protein from murine milk. J Biol Chem. Nov. 25, 1981;256(22):11509-16.

Pinkert et al., An albumin enhancer located 10 kb upstream functions along with its promoter to direct efficient, liver-specific expression in transgenic mice. Genes Dev. May 1987;1(3):268-76.

Potrykus, Gene transfer to plants: Assessment of published approaches and results. Annu. Rev. Plant Physiol.Plant Mol.Biol. 1991;42:205-225.

Ritchie et al., *Agrobacterium tumefaciens*-mediated expression of *gusA* in maize tissues. Transgenic Research. 1993;2:252-265.

Rosen et al., Membrane receptors and cellular recognition. Czech et al., eds., 1984. Alan R. Liss, Inc. NY:385-396.

Rosen et al., UCLA Symp Mol Cell Biol New Ser. 23 1985:385-98. Chem Abst 104:15909.

Rubinstein et al., Introduction of genes into preimplantation mouse embryos by use of a defective recombinant retrovirus. PNAS. 1986;83:366-368.

Salamone et al., High level expression of bioactive recombinant human growth hormone in the milk of a cloned transgenic cow. J Biotechnol. Jul. 13, 2006;124(2):469-72. Epub May 23, 2006.

Sargent et al., Fine structure and evolution of the rat serum albumin gene. Mol Cell Biol. Oct. 1981;1(10):871-83.

Sargent et al., The rat serum albumin gene: analysis of cloned sequences. Proc Natl Acad Sci U S A. Jul. 1979;76(7):3256-60.

Schäfer et al., T-DNA integration and expression in a monocot crop plant after induction of *Agrobacterium*. Nature. 1987;327:529-532.

Schell et al., Ti plasmids as experimental gene vectors for plants. Proceedings of the Miami Winter Symposia. Jan. 1983;20:191-209.

Schmeck, In the Gene Lab, Scientists Manipulate Codes of Life. The New York Times, sec. c, p. 1, Jan. 21, 1986.

Shamay et al., Expression of the whey acidic protein in transgenic pigs impairs mammary development. Transgenic Res. May 1992;1(3):124-32.

Shaw et al., Engineering bacteria and plants for enhanced nitrogen fixation. Proceedings of the 12$^{th}$ International Congress of Soil Science. New Delhi. 1982:54-68.

Smith, Commercial exploitation of transgenics. Biotechnol Adv. 1994;12(4):679-86.

Stromqvist et al., Recombinant human extracellular superoxide dismutase produced in milk of transgenic rabbits. Transgenic Res. Jul. 1997;6(4):271-8.

Sun et al., Intervening sequences in a plant gene—comparison of the partial sequence of cDNA and genomic DNA of French bean phaseolin. Nature. Jan. 1981;289:37-41.

Swift et al., Tissue-specific expression of the rat pancreatic elastase I gene in transgenic mice. Cell. Oct. 1984;38(3):639-46.

Tabe et al., Segregation of mutant ovalbumins and ovalbumin-globin fusion proteins in *Xenopus oocytes*. Identification of an ovalbumin signal sequence. J Mol Biol. Dec. 15, 1984;180(3):645-66.

Thepot et al., Rabbit whey acidic protein gene upstream region controls high-level expression of bovine growth hormone in the mammary gland of transgenic mice. Mol Reprod Dev. Nov. 1995;42(3):261-7.

Van Brunt, Molecular farming: transgenic animals as bioactors. Biotechnology. 1988;6:1149-1154.

Wall, Transgenic livestock: Progress and prospects for the future. Theriogenology. 1996;45(1):57-68.

Wall et al., Development of porcine ova that were centrifuged to permit visualization of pronuclei and nuclei. Biol Reprod. Apr. 1985;32(3):645-51.

Wall et al., High-level synthesis of a heterologous milk protein in the mammary glands of transgenic swine. Proc Natl Acad Sci U S A. Mar. 1, 1991;88(5):1696-700.

Walstra and Jenness, Dairy Chemistry and Physics. John Wiley & Sons, 1984.

Ward et al., The commercial and agricultural applications of animal transgenesis. Mol Biotechnol. Oct. 1995;4(2):167-78. Review.

Wei et al., Production of human surfactant protein C in milk of transgenic mice. Transgenic Res. Jul. 1995;4(4):232-40.

Westphal et al., Promoter sequences of murine alpha A crystallin, murine alpha 2(I) collagen or of *avian sarcoma* virus genes linked to the bacterial chloramphenicol acetyl transferase gene direct tissue-specific patterns of chloramphenicol acetyl transferase expression in transgenic mice. Cold Spring Harb Symp Quant Biol. 1985;50:411-6.

Wilmink et al., Expression of the GUS-gene in the monocot tulip after introduction by particle bombardment and *Agrobacterium*. Plant Cell Reports. 1992;11:76-80.

Wilmut et al., Production of pharmaceutical proteins in milk. Experientia. Sep. 15, 1991;47(9):905-12. Review.

Wilmut et al., Strategies for production of pharmaceutical proteins in milk Reprod Fertil Dev. 1994;6(5):625-30. Review.

Wilmut et al., A Revolution in Animal Breeding. New Scientist. Jul. 7, 1988:56-59.

Yom et al., Genetic engineering of milk composition: modification of milk components in lactating transgenic animals. Am J Clin Nutr. Aug. 1993;58(2 Suppl):299S-306S. Review.

Zambryski et al., Ti plasmid vector for the introduction of DNA into plant cells without alteration of their nromal regeneration capacity. EMBO J. 1983;2(12):2143-2150.

\* cited by examiner

TRANSGENIC ANIMALS SECRETING DESIRED PROTEINS INTO MILK

The present Application is a DIV of U.S. application Ser. No. 07/441,785, filed on Nov. 27, 1989, now abandoned, which is a DIV of U.S. application Ser. No. 06/849,815, filed on Apr. 9, 1986, now abandoned.

BACKGROUND OF THE INVENTION

This invention relates to transgenic animals.

It is possible to insert foreign genes into vertebrate embryos, and for these genes to be incorporated into the genome of the resulting animal. Insertion of the foreign genes has been carried out mechanically (by microinjection), and with the aid of retrovirus vectors (for example, as is described in Huszar et al. (1985) P.N.A.S. U.S.A 82, 8587). The animals resulting from this process are termed "transgenic." The foreign genes can be sexually transmitted through subsequent generations and are frequently expressed in the animal. In some instances the proteins encoded by the foreign genes are expressed in specific tissues. For example, the metallothionein promoter has been used to direct the expression of the rat growth hormone gene in the liver tissue of transgenic mice (Palmiter et al., 1982 Nature 300:611). Another example is the elastase promoter, which has been shown to direct the expression of foreign genes in the pancreas (Ornitz et al., 1985 Nature 313:600). Developmental control of gene expression has also been achieved in transgenic animals, i.e., the foreign gene is transcribed only during a certain time period, and only in a particular tissue. For example, Magram et al. (1985, Nature 315:338) demonstrated developmental control of genes under the direction of a globin promoter; and Krumlauf et al. (1985, Mol. Cell. Biol. 5:1639) demonstrated similar results using the alpha-feto protein minigene.

SUMMARY OF THE INVENTION

In general, the invention features a DNA sequence containing a gene encoding a protein, the gene being under the transcriptional control of a mammalian milk protein promoter which does not naturally control the transcription of the gene, the DNA sequence further including DNA enabling secretion of the protein; e.g., a secretion signal-encoding sequence interposed between the gene and promoter. The promoter can be that of a milk serum protein or a casein protein, although milk serum proteins are preferred, as will be discussed in more detail below. (As used herein, "gene" refers to both genomic DNA sequences and cDNA sequences.)

The invention permits the production of any desired protein in an easily maintained stable, portable culture system, i.e., a living domesticated mammal, which is capable not only of producing the desired protein, but preferably of passing on the ability to do so to its female offspring as well. Secretion of the protein into the host mammal's milk facilitates purification and obviates removal of blood products and culture media additives, some of which can be toxic or carcinogenic. More importantly, protein yields will be high and production will be more cost effective and efficient.

Other features and advantages of the invention will be apparent from the following description of the preferred embodiments thereof, and from the claims.

DESCRIPTION OF THE PREFERRED EMBODIMENTS

The drawings will first briefly be described.

Drawings

DNA SEQUENCE ELEMENTS

Promoter

The milk protein promoter can be derived from any mammalian species, and can be any promoter naturally associated with any protein which is normally secreted into mammalian milk. Generally, milk proteins are classified as the caseins, which are defined herein as the milk proteins which are present in milk in the form of micelles, and which are removed from skim milk by clotting with rennet; and the milk serum proteins, which are defined herein as the non-casein milk proteins. Whey proteins constitute the predominant fraction of the milk serum proteins, and in rodents include the protein known as whey acid protein. Whey acid protein ("WAP") is named based on its acidic isoelectric point (Piletz (1981) J. Biol. Chem. 256: 11509). Another example of a milk serum protein described in the literature is α-lactalbumin (described, along with mouse WAP, in Hennighausen and Sippel (1982) Eur. J. Biochem. 125, 131). Milk proteins are discussed in detail in Walstra and Jenness *Dairy Chemistry and Physics* (John Wiley & Sons 1984).

Generally, milk serum protein promoters are preferable to casein promoters in the present invention because caseins generally are produced in female mammals during pregnancy as well as after birth, while WAP is expressed primarily during post-partum lactation. This difference is of potential importance for two reasons. First, pre-birth production of the desired protein under the transcriptional control of a casein promoter could be wasteful, since the protein cannot be isolated from milk until it is secreted into the milk post-partum. Second, where the desired protein is toxic in large amounts (human tissue plasminogen activator (t-PA) is an example), a build-up of the protein in the tissues prior to lactation could be deleterious to the health of the host mammal. An additional advantage of some whey promoters such as the WAP promoter is that they are strong promoters, as evidenced by the large amounts of some whey proteins present in milk. Casein promoters also have this advantage.

Milk protein genes from which promoters, in addition to the WAP promoters, can be isolated, can be obtained in the same manner in which the WAP genes were isolated, as described in Hennighausen and Sippel, id, and Campbell et al. (1984) Nucleic Acids Research 12, 8685. The method generally involves isolating the mRNA from a lactating mammary gland, constructing a cDNA library from the mRNA, screening the library for the particular milk protein cDNA being sought, cloning that cDNA into vectors, and using the appropriate cDNA as a probe to isolate the genomic clone from a genomic library. A sequence upstream from the transcription start site in the genomic clone constitutes a putative "promoter", a genomic sequence preceeding the gene of interest and presumed to be involved in its regulation. The promoter may be isolated by carrying out restriction endonuclease digestions and subcloning steps. Promoters need not be of any particular length nor to have directly shown any properties of regulation. The mouse WAP promoter was isolated as a 2.6 kb EcoRI-KpnI fragment immediately 5' to the WAP signal sequence.

Desired Protein

Any desired protein can be produced according to the invention. Preferred proteins are proteins useful in the treatment, prevention, and/or diagnosis of human disease; examples are t-PA and hepatitis B surface antigen. The invention is particularly useful for proteins which must be produced on a large scale to be economical, e.g., industrial enzymes and animal proteins.

Signal Sequence

It is necessary, for secretion of the desired protein into the milk of the host mammal, that the DNA sequence containing the gene for the desired protein include DNA which, when translated, causes the protein to be secreted out of the mammary tissue into the milk. Without such a sequence, the desired protein would remain in the mammary tissue, from which purification would be difficult, and would require sacrifice of the host animal. This DNA can encode a hydrophobic secretion signal which is cleaved during secretion. The signal sequence can be that which is naturally associated with the desired protein, if the protein is normally secreted (e.g., t-PA). Alternatively, the signal encoding sequence can be that of the milk protein providing the promoter, i.e., when the milk protein gene is digested and the promoter isolated, a DNA fragment is selected which includes both the promoter and the signal encoding sequence directly downstream from the promoter. Another alternative is to employ a signal encoding sequence derived from another secreted protein, which is neither the milk protein normally expressed from the promoter nor the desired protein.

Termination Site

Preferably there is located within or downstream from the 3' end of the desired gene a termination site. This site may be provided by sequences in the gene itself, or may need to be added. If the sequence is to be added, a preferred sequence is provided by the polyadenylation sequence of the virus SV40, as will be described in greater detail below.

Methods

Genetic Manipulations

Generally, all DNA manipulations used in the genetic constructions of the invention are carried out using conventional techniques, as described, e.g., in Maniatis et al. *Molecular Cloning: A Laboratory Manual* (Cold Spring Harbor Laboratory, 1982).

Introduction of DNA into Embryos

Once the genetic constructions have been produced in vectors, e.g., plasmids, the promoter-signal sequence-desired protein-termination sequence DNA fragment is excised and then introduced into the desired mammalian embryo using, e.g., retroviruses or standard microinjection methods such as are described in Kraemer et al. (1985), Costantini and Jaenisch, eds., *Genetic Manipulaton of the Early Mammalian Embryo*, Cold Spring Harbor Laboratory (bovine embryo microinjection); Hammer et al. (1985) Nature 315, 680 (rabbit, sheep, and porcine embryo microinjection); and Gordon and Ruddle (1984) Methods in Embryology 101, 411 (mouse embryo microinjection). Micro-injection is preferably carried out on an embryo at the one-cell stage, to maximize both the chances that the injected DNA will be incorporated into all cells of the animal, including mammary tissue, and that the DNA will also be incorporated into the germ cells, so that the animal's offspring will be transgenic as well. Microinjection is a standard technique which involves, briefly, isolating fertilized ova, visualizing the pronucleus, and then injecting the DNA into the pronucleus by holding the ova with a blunt holding pipette of a diameter on the order of 50 µm, and using a sharply pointed pipette of a diameter on the order of 1.5 µm to inject buffer-containing DNA into the pronucleus. Following microinjection, the transgenic female animals are allowed to become sexually mature, mated, and milk collected postpartum.

Preferred host mammals are those which are already bred for large volume milk production, e.g., cows, sheep, goats, and pigs.

t-PA Production

There will now be described the construction of plasmid DNA in which the gene encoding human uterine t-PA, including the signal encoding sequence, is under the transcriptional control of the mouse WAP promoter, and has at its 3' end the SV40 polyadenylation site. This DNA was made from two intermediate plasmids, one carrying the mouse WAP promoter and one carrying the t-PA signal and structural sequences, as well as the SV40 polyadenylation site.

The WAP promoter containing plasmid pWAP-CAT (FIG. 2, obtained from Lothar Hennighausen, National Institutes of Health) was derived from a plasmid made according to the methods described in Hennighausen and Sippel (1982) Eur. J. Biochem. 125, 131; and Campbell et al. (1984) Nucleic Acids Research 12, 8685. In addition to containing the mouse WAP promoter, pWAP-CAT contains a gene which, for present purposes, is irrelevant: the CAT (chloramphenical acetyltransferase) gene, which does not form a part of the final DNA sequence which is microinjected.

Figure 2:
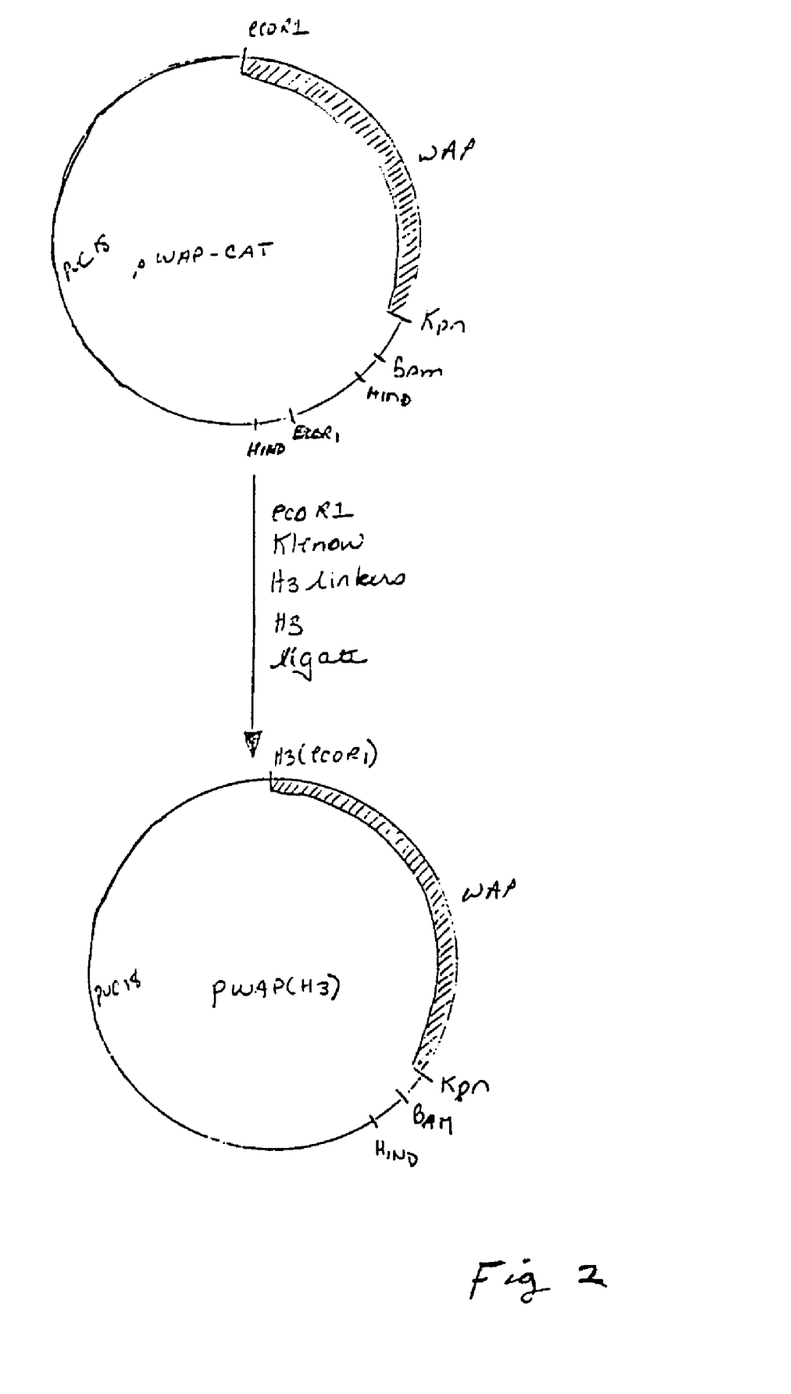
FIG. 2 is a diagrammatic representation of the construction of an intermediate vector of the invention, pWAP ($H_3$).

Still referring to FIG. 2, pWAP-CAT was modified to convert the EcoRI site to a HindIII site using Klenow and HindIII linkers.

Figure 1:
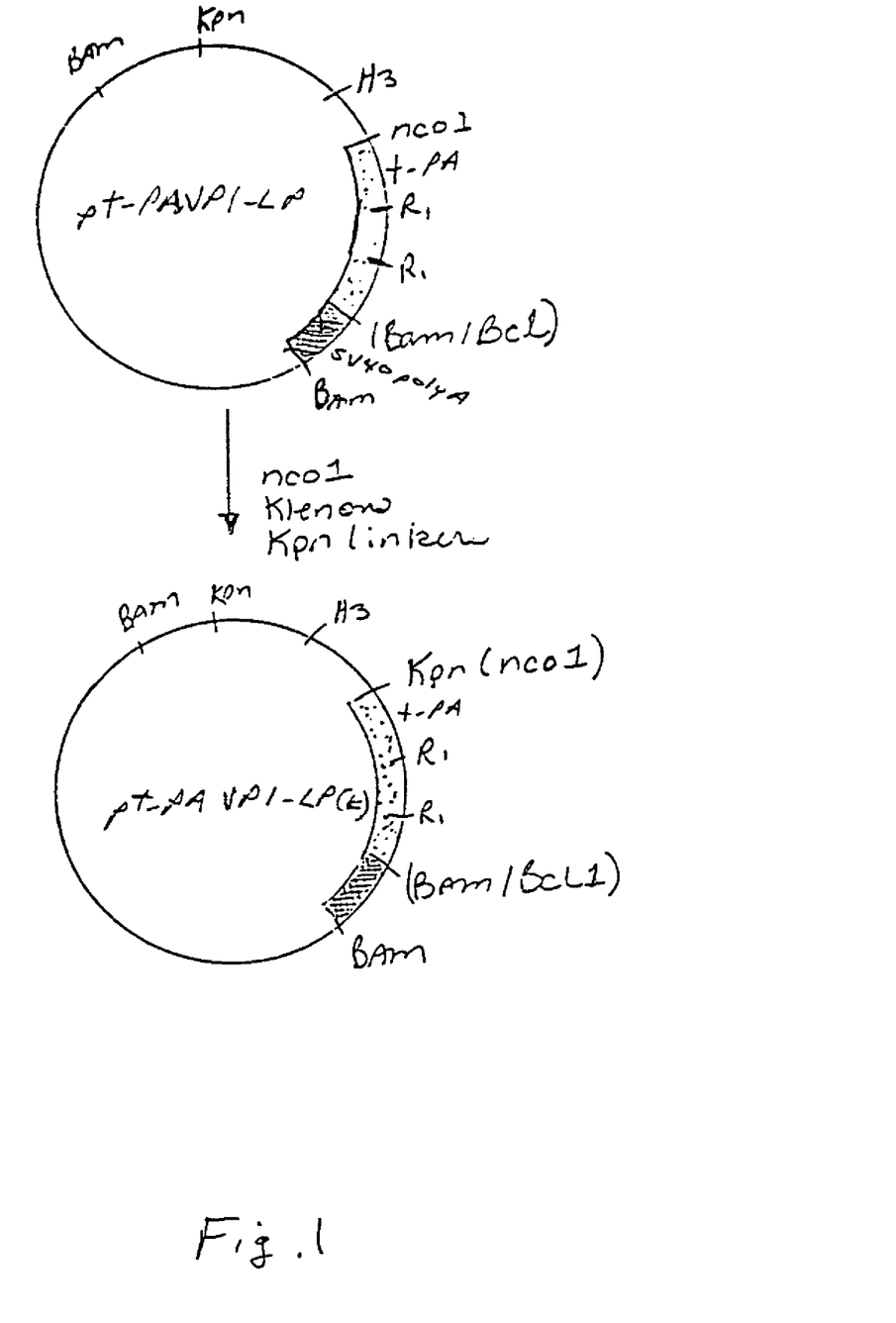
FIG. 1 is a diagrammatic representation of the construction of an intermediate vector of the invention, pt-PA VP1-LP(K).

The t-PA-containing plasmid pt-PA-VP1-LP(K) (FIG. 1) was derived from pt-PAVPI-LP, containing the t-PA gene (including the t-PA signal encoding sequence) and SV40 polyadenylation site, by modifying the unique NcoI site at the 5' end of the t-PA gene using NcoI endonuclease and Klenow and adding Kpn linkers to produce a KpnI site.

Figure 3:
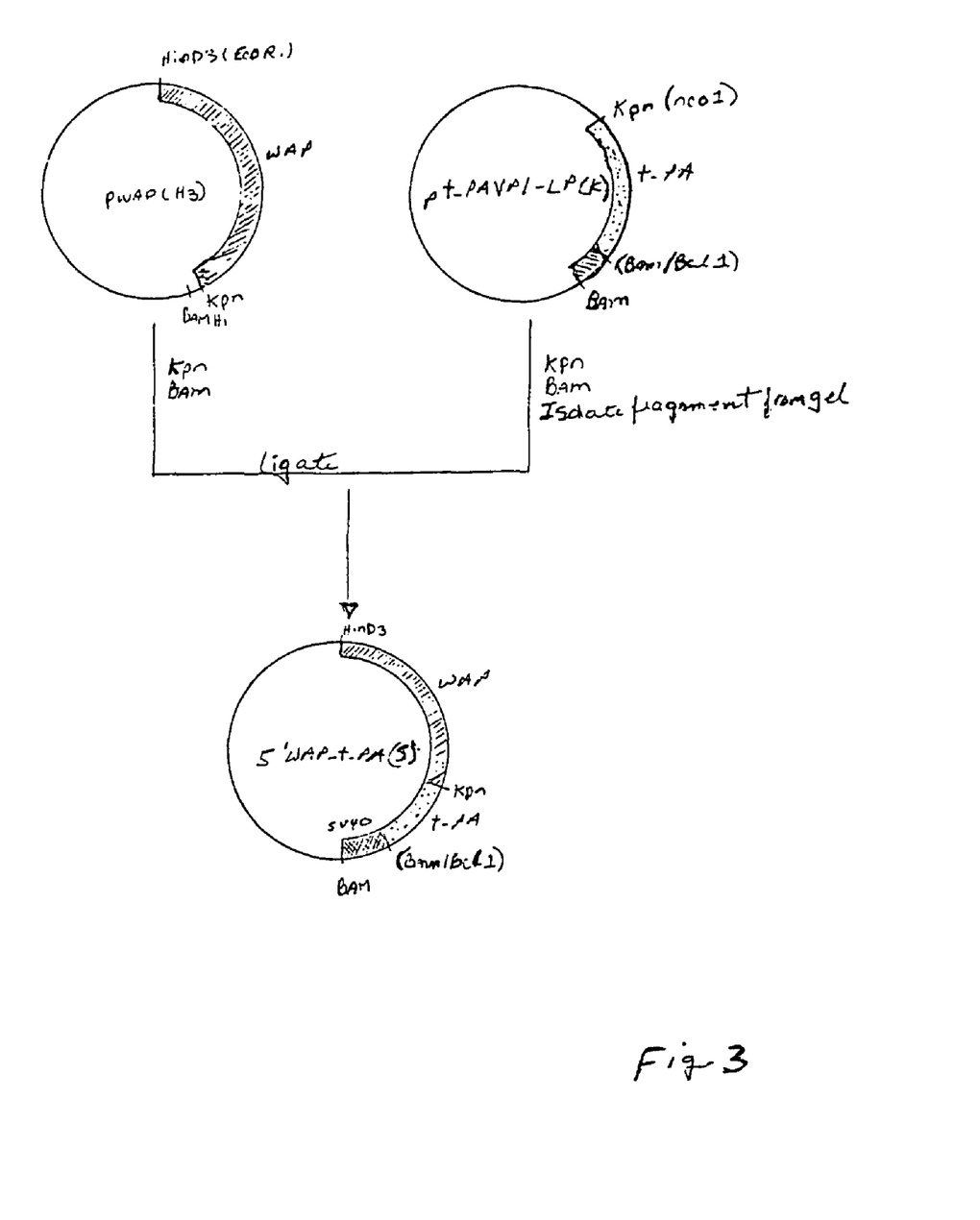
FIG. 3 is a diagrammatic representation of the construction of a vector of the invention, pWAP-t-PA(S).

Referring to FIG. 3, the KpnI-BamHI fragment of pt-PA VP1-LP(K), containing the t-PA gene and SV40 sequences, was isolated and ligated to BamHI-KpnI treated pWAP(H3) to form pWAP-tPA (S), which was then transformed into a TET-sensitive derivative of *E. coli* strain MC1061. This transformed strain, containing plasmid DNA in which the HindIII-BamHI fragment contains the t-PA gene including the t-PA signal encoding sequence under the transcriptional control of the WAP promoter and followed by the SV40 polyadenylation site, has been deposited in the American Type Culture Collection and given ATCC Accession No. 67032. Applicants' assignee, Integrated Genetics, Inc., acknowledges its responsibility to replace this culture should it die before the end of the term of a patent issued hereon, and its responsibility to notify the ATCC of the issuance of such a patent, at which time the deposit will be made available to the public. Until that time the deposit will be made available to the Commissioner of Patents under the terms of 37 CFR §1.14 and 35 USC §112. Assignee agrees that this designated culture will be maintained throughout the effective life of a patent granted, for 30 years from the date of deposit, or for 5 years after the last request for the deposit after issuance of the patent, whichever is longer.

Production of milk into which t-PA has been secreted is carried out by excising the HindIII-BamHI fragment from the deposited strain and transferring it by microinjection or other means preferably into the one-cell embryo of a mammal according to conventional methods, as described above. Alternatively, though less desirably, the entire plasmid or other restriction fragments can be introduced into the embryos. Embryos are then nurtured to term in vivo. Animals born from such manipulated embryos are screened for the presence of introduced DNA in the genome, and expression of t-PA in the milk is screened for among transgenic, lactating females. The protein from the milk of the adult lactating female animal will be assayed for t-PA by conventional procedures.

Production of Hepatitis B Surface Antigen

Figure 5:
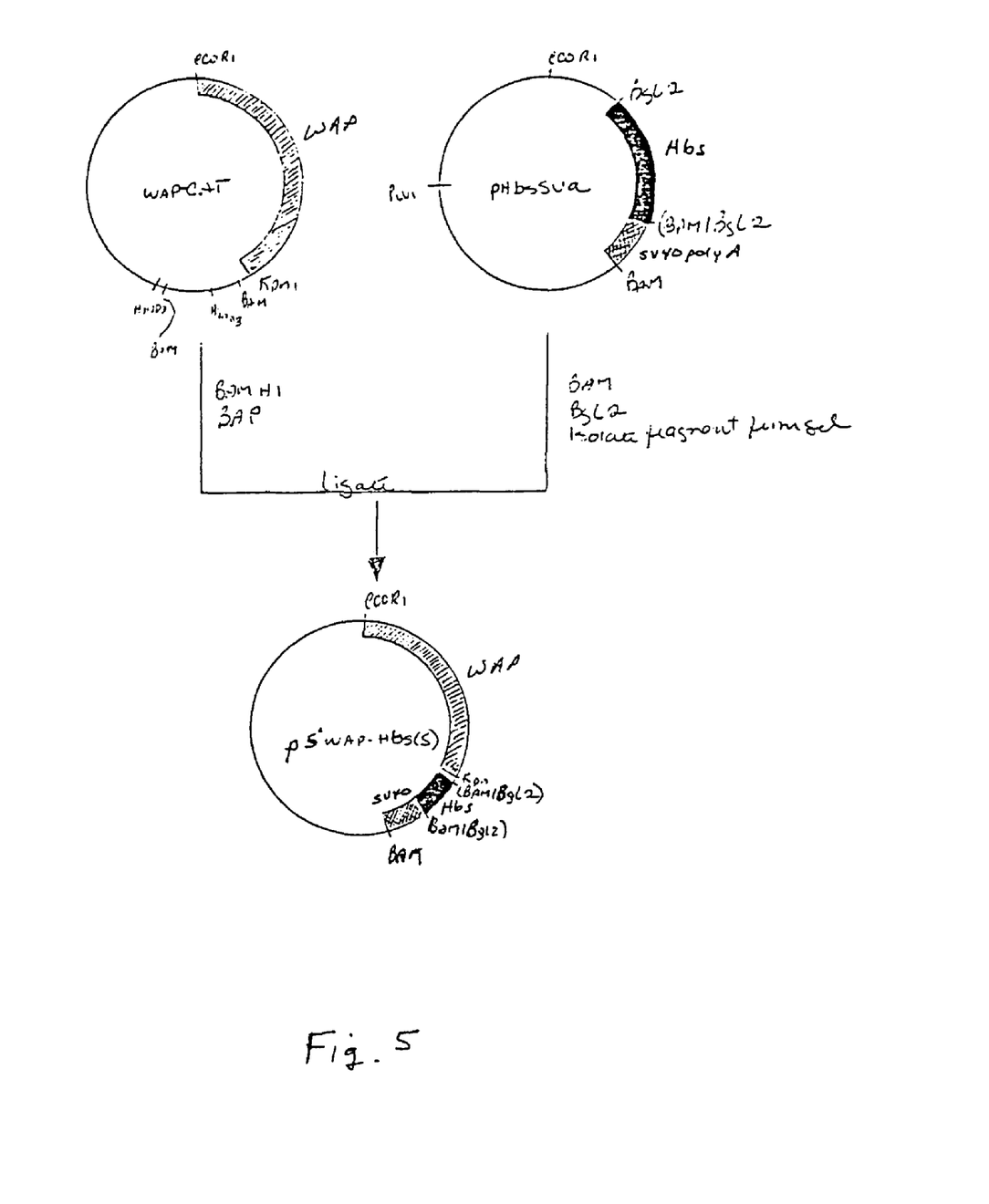
FIG. 5 is a diagrammatic representation of the construction of a vector of the invention, pWAP-Hbs(S).

Referring to FIG. 5, intermediate vectors pWAP-CAT and pHBsSVA were used to construct pWAP-Hbs(S), containing the gene for hepatitis B surface antigen, under the transcriptional control of the WAP promoter and followed by the SV40 polyadenylation site.

Figure 4:
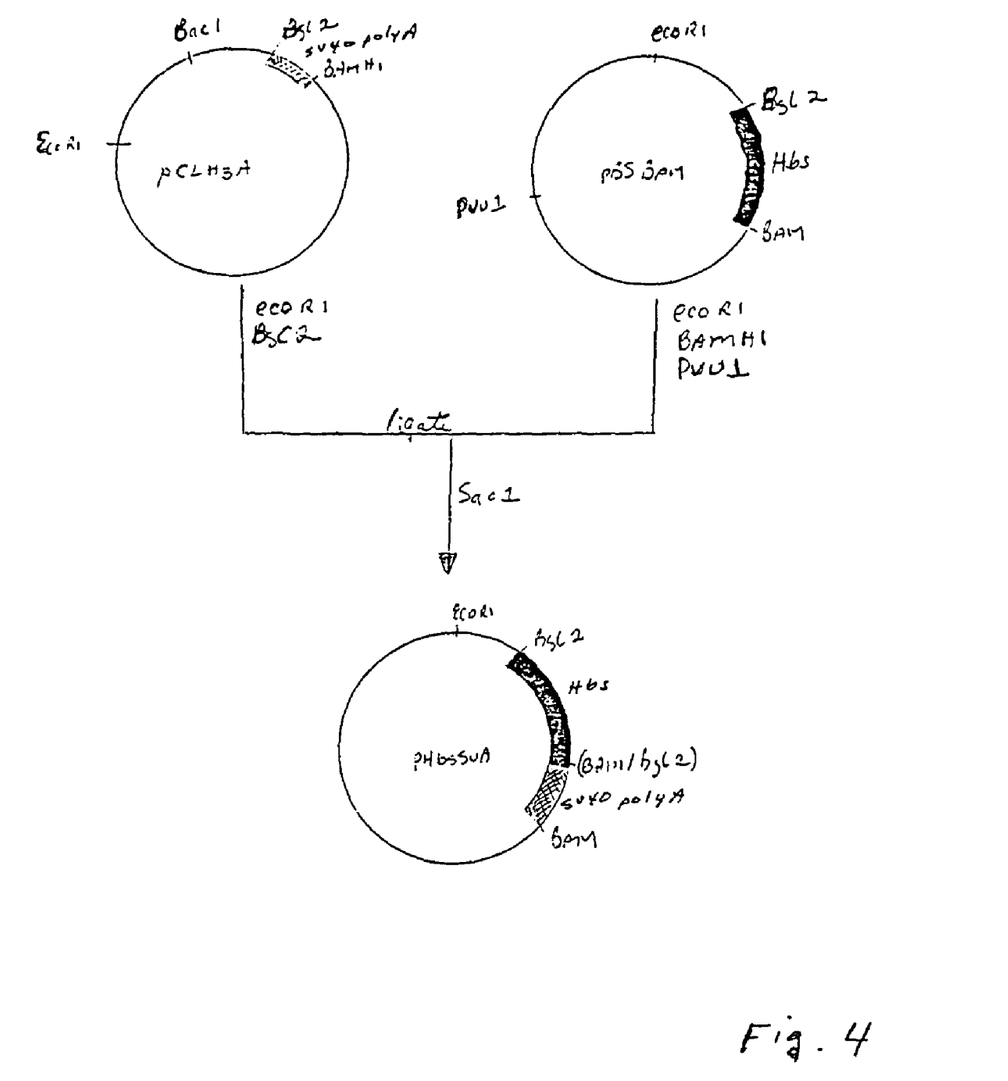
FIG. 4 is a diagrammatic representation of the construction of an intermediate vector of the invention, pHbsSVA.

The plasmid pWAP-CAT is described above. Plasmid pHb-sSVA was constructed as illustrated in FIG. 4. pCLH$_3$A, containing the SV40 polyadenylation sequence, was restricted with EcoRI, SacI, and BglII. pBSBam, containing the gene for hepatitis B surface antigen, was cut with EcoRI, BamHI and PvuI, and the two mixtures ligated to give pHb-sSVA, in which the SV40 sequence was positioned at the 3' end of the Hbs gene, on a BamHI-BglII fragment. This fragment was then ligated (FIG. 5) to BamHI and bacterial alkaline phosphatase-treated pWAP-CAT, transformed into *E. coli* strain MC1061, and the plasmid pWAP-Hbs(S) isolated.

The BamHI-EcoRI fragment of WAP-Hbs(S) can be excised and used as described above to produce hepatitis B surface antigen. Alternatively, though less desirably, the entire plasmid or other restriction fragments can be introduced into the embryos. Embryos are then nurtured to term in vivo. Animals born from such manipulated embryos are screened for the presence of introduced DNA in the genome, and expression of hepatitis B surface antigen in the milk is screened for among transgenic, lactating females. pWAP-Hbs(S) has been deposited in the American Type Culture Collection and given ATCC Accession No. 67033. Applicants' assignee, Integrated Genetics, Inc., acknowledges its responsibility to replace this culture should it die before the end of the term of a patent issued hereon, and its responsibility to notify the ATCC of the issuance of such a patent, at which time the deposit will be made available to the public. Until that time the deposit will be made available to the Commissioner of Patents under the terms of 37 CFR §1.14 and 35 USC §112. Assignee agrees that this designated culture will be maintained throughout the effective life of a patent granted, for 30 years from the date of deposit, or for 0.5 years after the last request for the deposit after issuance of the patent, whichever is longer.

Both pWAP-Hbs(S) and pWAP-t-PA(S) can be used as cassette vectors in which the hepatitis B surface antigen gene or the t-PA gene can be excised and replaced, using conventional methods, with any desired gene. If desired, the signal encoding sequence from pWAP-t-PA(S) can be left in the vector, and a gene lacking such a sequence inserted downstream of and in frame with it. Alternatively, the signal sequence from pWAP-t-PA(S) or pWAP-Hbs(S) can be removed along with the structural gene and the signal encoding sequence of the substituted gene employed. In addition, the WAP promoter alone can be excised and inserted into another desired expression vector.

Purification and Use

The proteins produced according to the invention are purified from the milk into which they have been secreted and used for their known purposes.

Hepatitis B surface antigen is useful in the production of hepatitis B vaccine, as described in Hsiung et al. U.S. Ser. No. 570,940, assigned to the same assignee as the present application, hereby incorporated by reference.

t-PA is useful in the treatment of thrombolytic disease in which fibrin clot lysis is necessary, as described in Wei et al. U.S. Ser. No. 782,686, assigned to the same assignee as the present application, hereby incorporated by reference. That patent application also describes general purification techniques which will be useful for milk-secreted proteins.

Stability in Milk

Table I below shows that, despite the presence in milk of numerous proteases, recombinant t-PA is stable when added to raw goat milk and incubated at 20° or 37° C. for 24 hours, with no evidence of loss of activity, as measured using the standard fibrin plate test (results not shown in Table I) or the amidolytic assay described in Wei et al., id. Similarly, recombinant hepatitis B surface antigen was found to be stable for at least 24 hours in raw goat milk (data not shown).

TABLE I

| Amidolytic assay for TPA | | | |
| --- | --- | --- | --- |
| | Incubation Time | Temperature | Units/ml |
| Goat milk alone | — | — | <20, <20 |
| Goat milk & TPA | 0 | — | 437, 368 |
| Goat milk & TPA | 24 hours | 20° C. | 419, 434 |
| Goat milk & TPA | 24 hours | 37° C. | 467, 507 |

Other Embodiments

Other embodiments are within the following claims. For example, other milk serum protein promoters can be used in place of the mouse WAP promoter, and the promoter can be derived from any mammalian species. For example, milk serum protein promoters such as that of β-lactoglobulin can be used, and the rat, rather than mouse, WAP promoter can be used; the rat WAP promoter is described in Campbell et al., id. Although less desirable than milk serum protein promoters, casein promoters can be used as well. The protein produced using the invention can be any desired protein of therapeutic or industrial importance.

The invention claimed is:

1. A DNA construct comprising a gene encoding a protein, said gene being under transcriptional control of a mammalian milk protein promoter sequence which does not naturally control transcription of said gene, said DNA construct further comprising DNA encoding a peptide enabling secretion of said protein.

2. The DNA construct of claim 1, wherein said secretion enabling peptide comprises a secretion signal peptide which is cleaved from said secretion protein.

3. The DNA construct of claim 1, wherein said DNA encoding a peptide enabling secretion of said protein is the signal encoding sequence naturally associated with said gene encoding said protein.

4. The DNA construct of claim 1, wherein said DNA encoding a peptide enabling secretion of said protein is the signal encoding sequence naturally associated with said mammalian milk protein promoter.

5. The DNA construct of claim 1, wherein said DNA sequence includes a transcriptional stop sequence.

6. The DNA construct of claim 5, wherein said stop sequence comprises the SV40 virus polyadenylation site.

7. The DNA construct of claim 1, wherein said gene encodes human tissue plasminogen activator or hepatitis B surface antigen.

8. The DNA construct of claim 1, wherein said milk protein is a milk serum protein.

9. The DNA construct of claim 8, wherein said milk serum protein is alpha-lactalbumin.

10. The DNA construct of claim 1, wherein the mammalian milk protein promoter sequence is the sequence of a milk serum protein promoter.

11. The DNA construct of claim 10, wherein the milk serum protein promoter is an α-lactalbumin promoter.

12. The DNA construct of claim 10, wherein the milk serum protein promoter is a β-lactoglobulin promoter.

13. The DNA construct of claim 1, wherein the mammalian milk protein promoter sequence is the sequence of a casein protein promoter.

* * * * *